United States Patent
Je et al.

(10) Patent No.: US 7,620,149 B2
(45) Date of Patent: Nov. 17, 2009

(54) CHARACTERIZATION OF THREE-DIMENSIONAL DISTRIBUTION OF DEFECTS BY X-RAY TOPOGRAPHY

(75) Inventors: Jung Ho Je, Gyeongsangbuk-do (KR); Jae Mok Yi, Gyeongsangbuk-do (KR)

(73) Assignees: Postech Foundation (KR); Postech Academy-Industry Foundation (KR)

( * ) Notice: Subject to any disclaimer, the term of this patent is extended or adjusted under 35 U.S.C. 154(b) by 0 days.

(21) Appl. No.: 12/087,402

(22) PCT Filed: Jan. 6, 2006

(86) PCT No.: PCT/KR2006/000062
§ 371 (c)(1),
(2), (4) Date: Jul. 3, 2008

(87) PCT Pub. No.: WO2007/078023
PCT Pub. Date: Jul. 12, 2007

(65) Prior Publication Data
US 2009/0034681 A1   Feb. 5, 2009

(51) Int. Cl.
*G01N 23/207* (2006.01)
(52) U.S. Cl. .......................... 378/74; 378/71
(58) Field of Classification Search ............ 378/70, 378/71, 73–74, 79, 82, 83, 84, 85, 87, 88
See application file for complete search history.

(56) References Cited

U.S. PATENT DOCUMENTS

| | | | |
|---|---|---|---|
| 4,580,054 A | 4/1986 | Shimoni et al. | |
| 6,751,287 B1 * | 6/2004 | Kalyon et al. | 378/71 |
| 6,867,862 B2 | 3/2005 | Nikoonahad | |
| 2003/0128809 A1 * | 7/2003 | Umezawa et al. | 378/70 |
| 2009/0103680 A1 * | 4/2009 | Park et al. | 378/73 |

FOREIGN PATENT DOCUMENTS

JP    06-027049 A    2/1994

* cited by examiner

*Primary Examiner*—Hoon Song
(74) *Attorney, Agent, or Firm*—Harness, Dickey & Pierce, P.L.C.

(57) ABSTRACT

Provided is a method of determining a three-dimensional distribution of structural defects in a single crystal material, the method comprising: (a) disposing a single crystal sample on a holder, the sample being set to a symmetric reflection in the Bragg Geometry; (b) projecting a beam of incident x-rays on a predetermined crystal plane in the sample and reflecting the x-rays while the sample is azimuthally rotating with respect to an normal axis, the normal axis being perpendicular to the predetermined crystal plane; (c) obtaining geometrical measured values of a two-dimensional configuration of defects on the detector plane of a CCD detector; and (d) determining the three-dimensional distribution of the defects in the sample by formulating a geometrical relation between a three-dimensional configuration of defects on the sample and the geometrical measured values of the two-dimensional configuration of defects on the detector plane.

7 Claims, 3 Drawing Sheets

(a)

(b)

CHARACTERIZATION OF THREE-DIMENSIONAL DISTRIBUTION OF DEFECTS BY X-RAY TOPOGRAPHY

BACKGROUND OF THE INVENTION

1. Field of the Invention

The present invention relates to nondestructive, quantitative determination of the three-dimensional distribution of the defects in single crystals.

2. Description of the Related Art

Characterization of the orientations and locations of dislocation lines in single crystals, together with the Burgers vectors, is an important issue not only for identifying the nature of dislocations but also for understanding the formation of local microstructure (lattice tilt, strain etc).

Quantitative determination of the three-dimensional distribution of the structural defects except dislocations is also necessary to identify the nature of defects and understand the formation of local microstructure.

Some X-ray topographic techniques, such as stereographic techniques in Laue (Lang, 1959a,b; Haruta, 1965) or Bragg (Vreeland, 1976) geometries, and the 'topo-tomographic' technique (Ludwig et al., 2001), are currently applied for qualitative determination of the orientations and locations of dislocation lines.

In the stereographic techniques such as Laue, and Bragg, white beam x-rays are used and photographic x-ray film is used to obtain Laue spots. From various Laue spots, some topographs are obtained by optical microscope with magnification. By comparing images of defects on the topographs, mainly topographs of different reflections, the distribution of defects is determined qualitatively.

Accordingly, the conventional techniques provide approximation on distribution of defects. They also require off-line processing work such as film development, etc.

In a topo-tomographic technique, the basic principle is 3-D reconstruction of defects from a thousand images of defects obtained by topographic rotation method. A monochromatic beam together with transmission geometry is used. However, the topo-tomographic technique requires that a special type of sample, for example, a small piece of sample or a stripe type of sample, appropriate for 360 degrees rotation of the sample, is required. This topo-tomographic technique is thus not applicable to a wafer type of sample. In addition, this technique needs a lot of time in performing a long data processing including a reconstruction work. Nevertheless, it may only provide qualitative information on distribution of defects.

On the other hand, recent developments of on-line high-resolution diffraction imaging, activated by using real-time imaging systems in conjunction with synchrotron radiation (Koch et al., 1998), have significantly facilitated the mapping of local microstructure by rocking curve imaging (Lübbert et al., 2000).

A straightforward correction between the local microstructure and the configuration of the dislocations involved is an issue of interest. For this work, the dislocation characterization that is experimentally compatible with the rocking curve imaging is required.

SUMMARY OF THE INVENTION

It is therefore an object of the present invention to provide a nondestructive, quantitative determination of the orientations and locations of dislocation lines in single crystals at high precision in a short time.

It is another object of the present invention to provide a method of determining quantitatively a three-dimensional distribution of structural defects in a single crystal material.

To achieve these objects, the present invention is based on using a symmetric reflection of Bragg geometry via azimuthal rotation of a sample and examining the defects in the sample. Accordingly, the present invention provides a method of determining a three-dimensional distribution of structural defects in a single crystal material, the method comprising: (a) disposing a single crystal sample on a holder, the sample being set to a symmetric reflection in the Bragg Geometry; (b) projecting a beam of incident x-rays on a predetermined crystal plane in the sample and reflecting the x-rays while the sample is azimuthally rotating with respect to an normal axis, the normal axis being perpendicular to the predetermined crystal plane; (c) obtaining geometrical measured values of defects on the detector plane of a CCD detector; and (d) determining the three-dimensional distribution of defects in the sample by formulating a geometrical relation between a three-dimensional configuration of defects on the sample and the geometrical measured values of a two-dimensional configuration of defects on the detector plane.

The defect preferably includes dislocations, inclusions, or voids.

The three-dimensional distribution preferably includes at least one selected from the group consisting of position, height, width, and length of the defect.

Preferably, in a projecting and reflecting step, the rotation of the sample performed by 45 degrees over a total range of 180 degrees.

The incident x-ray is preferred to be a monochromatic beam.

The x-rays preferably include synchrotron x-ray.

Preferably, the three-dimensional distribution of dislocations is crystallographic orientations and the lengths of the dislocations in the sample.

According to this invention, this technique may be performed easily on a conventional 4-circle diffractometer with a short time, at an on-line experiment. Quantitative information on defect distribution is obtained. There is also no limitation on sample geometry, and thereby any shapes of sample including a wafer type of sample may be in this technique.

BRIEF DESCRIPTION OF THE DRAWINGS

The above aspects and features of the present invention will be more apparent by describing certain embodiments of the present invention with reference to the accompanying figures, in which.

Herein, three representative dislocations, A-C, are indicated in each topograph. The rotation angles are marked.

Figure 3:
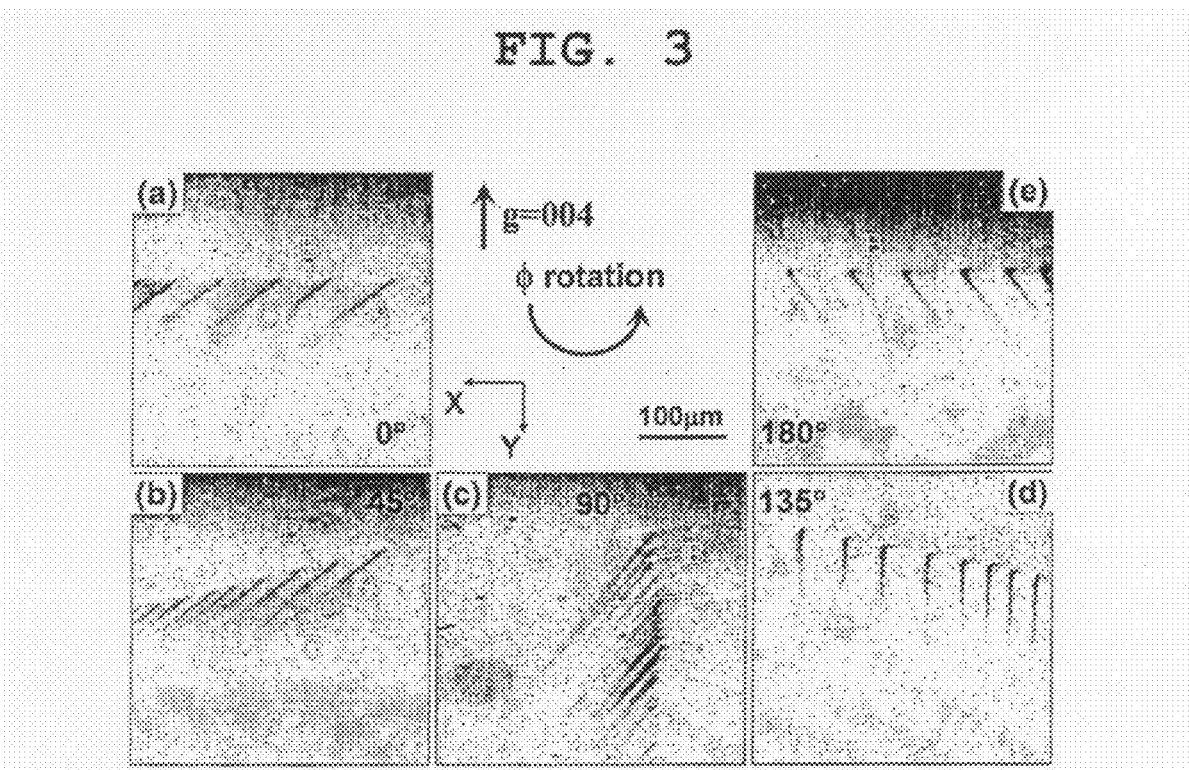
FIG. 3 shows a series of x-ray topographs obtained from the Si 004 reflection via the azimuthal rotation of the sample.
Figure 4:
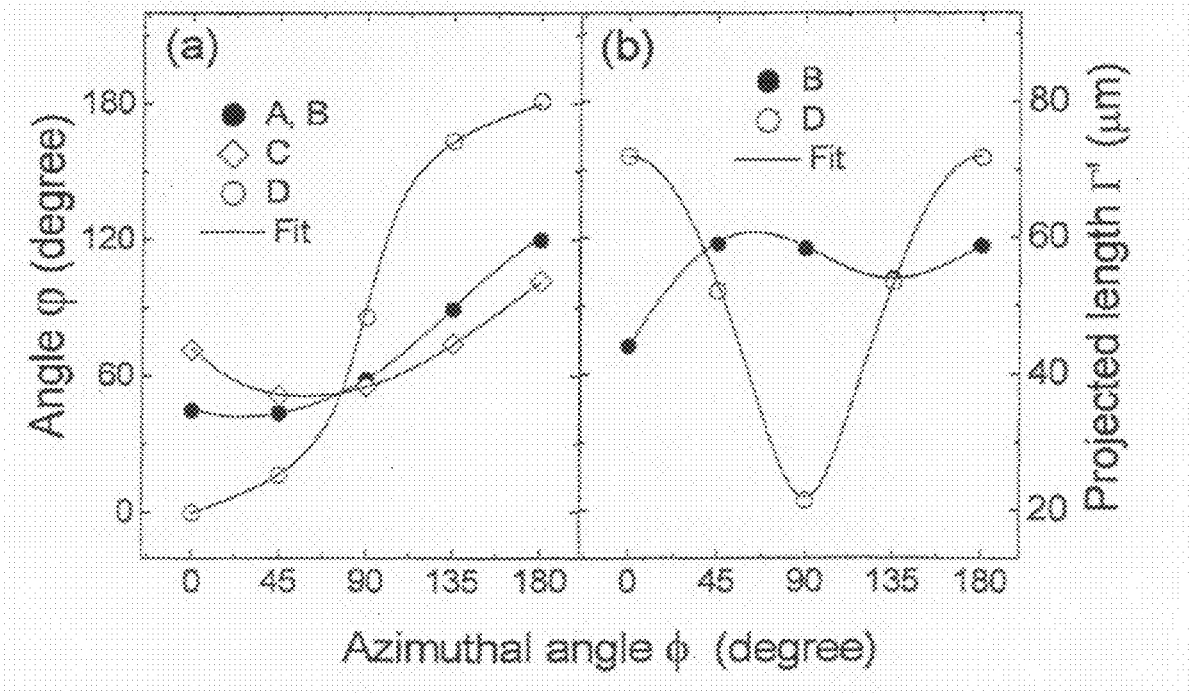

FIG. 4 is a graph showing a variation of (a) the angles—and (b) the projected lengths—as a function of the azimuthal rotation angle—obtained for the three dislocations, A-C and the virtual line (denoted D) connecting the two outcrops of A and B shown in FIG. 3.

Herein the solid lines are the results of a fit to the transformation formula.

DETAILED DESCRIPTION OF THE INVENTION

X-ray topography experiments were performed at the XOR 2-BM beamline of the Advanced Photon Source, USA.

A monochromatic beam is provided by a Si(111) double-bounce monochromator at 15 keV.

A lens-coupled high-resolution CCD camera system was used for imaging diffracted beam intensity. High-resolution imaging was achieved by focusing a visible light, produced by the diffracted beam striking a $CdWO_4$ scintillation crystal, through a 10× objective lens to yield 0.65 μm effective pixel resolution.

As a test sample, a Si (001) wafer of 0.75 mm thick is used to characterize the dislocations caused by thermal stress during heating of the wafer at 1323 K.

The lens-coupled CCD system is set up such that it is normal to the diffracted beam and is positioned 5 mm away from the sample.

The single crystal sample was set to a symmetric Si 004 reflection (θ=17.7°) in the Bragg geometry.

The Bragg geometry means that the incident beam, the normal to the reflecting plane and the diffracted beam are always coplanar and that the angle between the incident beam and the diffracted beam is always 2θ.

The single crystal sample is maintained in a fixed orientation with respect to a beam of x-rays. In this embodiment, the incident x-ray beam is directed at an angle of incidence θ(=17.7°) with respect to a reflecting plane (004) and is then directed at an angle of reflection θ(=17.7°) with respect to the reflecting plane (004) into the CCD system.

Further, according to this invention, the orientation of the sample is adjusted while an x-ray diffracted by the sample is detected by the CCD system. In this embodiment, the sample is oriented so that the [1 1̄ 0] direction of the sample crystal is perpendicular to a scattering plane defined by $k_i$ and $k_f$, where $k_i$ and $k_f$ are the incident and exit wavelengths, respectively. Accordingly, the scattering plane defined by the two beams involved is coplanar i.e., the above two beams and the normal to the reflecting plane (004) form a coplanar plane (1 1̄ 0). This angular position is designated as ø=0°, where ø is the azimuthal rotation angle around the diffraction vector g, which corresponds to the normal to the reflecting plane (004).

The sample is rotated about the chosen direction, i.e., a diffraction vector g, the axis normal to the reflecting plane (004).

A series of X-ray topographs are taken while rotating the azimuthal angle of the sample in 45° steps over a total range of 180°. Any angular step and range would provide a series of topographs, but we have noted empirically that 45° steps in the 180° range is optimum to reduce ambiguities in an image analysis. Specifically, the weak-beam technique (Authier, 2001) was applied for each topograph in order to narrow the width of dislocation images and to avoid the double contrast that appeared at the peak of the rocking curve of the sample. The typical exposure time for each topograph is a few seconds.

Description of the Transformation Formula

Since X-ray topography provides a two-dimensional (2-D) projection of the three-dimensional (3-D) configuration of a dislocation, it is very useful to formulate the geometrical relation between the configuration in the sample and the topograph (Miltat & Dudley, 1980; Yuan & Dudley, 1992).

Figure 1:
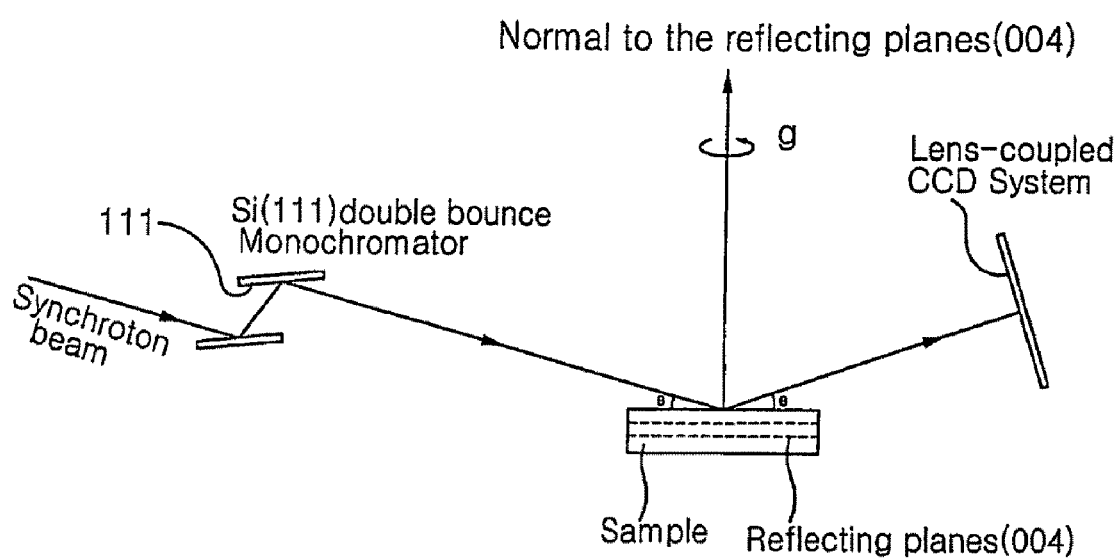
FIG. 1 is a schematic representation of an apparatus of quantitatively determining the orientations and locations of dislocations in single crystals according to one preferred embodiment of this invention, wherein the x-ray beam is incident from the left and is monochromatized by the Si(1,1,1) crystal. This beam is incident on the sample at an incident angle and is diffracted into a lens-coupled high-resolution CCD camera system. The diffracted beam is detected as an image on the CCD camera system.
Figure 2:
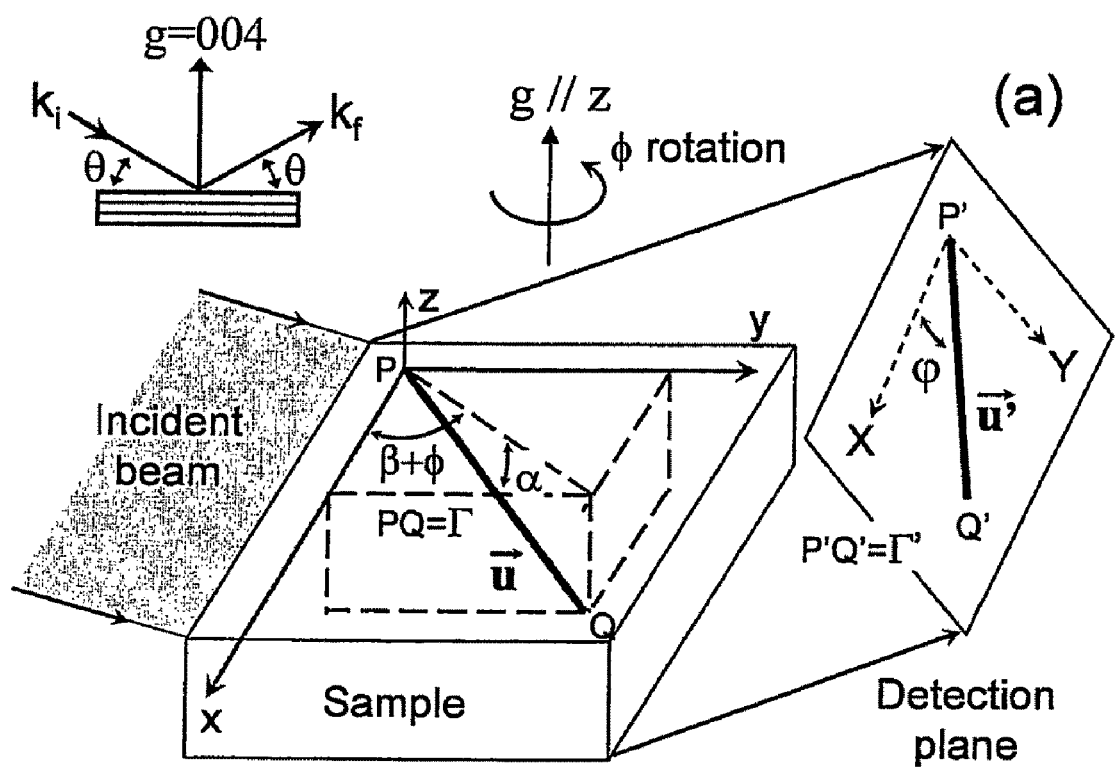
FIG. 2a is a schematic diagram showing an X-ray irradiation region of the sample to transform a dislocation (u) into its 2-D projection (u'). Herein dotted lines confine the sample volume illuminated by X-rays. The inset in the top-left of the figure shows the geometry of the experiment.
FIG. 2b is a schematic diagram of the components of u on the yz plane and the Y component of u'.
Figure 2:
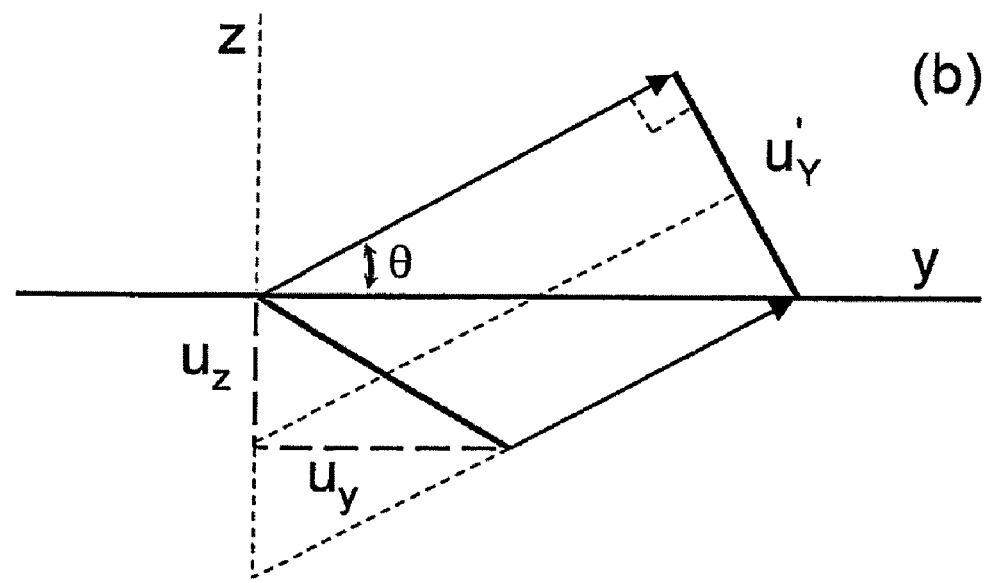

FIG. 2(a) shows a schematic diagram of the transformation of a dislocation configuration by X-ray topography after an azimuthal rotation ø of the sample. An xyz Cartesian coordinate system is defined such that the z axis is along the diffraction vector g and the yz plane coincides with the scattering plane. A dislocation is represented by a vector u.

$$u = (\Gamma \cos \alpha \cos(\beta+ø), \Gamma \cos \alpha \sin(\beta+ø), -\Gamma \sin \alpha) \quad (1)$$

Where α and β are two Euler angles at ø=0° and Γ is the length of the dislocation. On the other hand, the dislocation line measured in the detector plane is represented by a vector U', $$U' = (\Gamma' \cos \phi, \Gamma' \sin \phi) \quad (2)$$

in an XY Cartesian ordinate system, where φ is the angle of the line with respect to the X axis and Γ' is the length.

In the parallel beam approximation, $U'_x = U_x$. The coordinate transformation of $U_y$ and $U_z$ into $U'_Y$ is easily seen in FIG. 2(b), which shows the components of u on the yz plane and the Y component of U'. It is clear that $U'_Y$ is equal to the projection of $U_z$ and $U_y$ onto the detection plane that is normal to the diffracted beam.

Thus, the following relationship is obtained:

$$U' = (\Gamma' \cos\varphi, \Gamma' \sin\varphi) \quad (3)$$
$$= [\Gamma\cos\alpha\cos(\beta+ø), \Gamma\sin\alpha\cos\theta + \Gamma\cos\alpha\sin(\beta+ø)\sin\theta]$$

Consequently, the angular and length components of the transformation formula, $$\tan \phi = \tan \alpha \cos ø/\cos(\beta+ø) + \tan(\beta+ø)\sin \theta \quad (4)$$

And $$\Gamma'^2/\Gamma^2 = [=[\cos(\beta+ø)\cos \alpha]^2 + [\sin \theta \sin(\beta+ø)\cos \alpha + \cos \theta \sin \alpha]^2 \quad (5)$$

FIGS. 3(a) to 3(e) show the series of topographs obtained for the Si 004 reflection by the azimuthal ø rotation of the sample. The black lines represent the enhanced intensity of direct dislocation images. The variation of the two-dimensional configuration of the lines with the azimuthal rotation shows nonlinear features.

It is obvious that such nonlinear features result from the projection effect of the three-dimensional characteristics of the dislocation. An analytic approach is preferable to understand this behavior and to determine the configuration of the dislocation lines in the sample.

Quantitative analysis on the variation of the 2-D configuration of the lines for the three representative dislocation lines, A-C, and the virtual line (denoted D) connecting the two outcrops of A and B in FIGS. 3(a) to 3(e) is performed. The angles (φ) with respect to the horizontal X axis and the projected lengths (Γ') (for B and D) is measured by indexing two XY points of each line using an image analysis software.

FIGS. 4(a) and 4(b) represent the variation of the angles and the lengths, respectively, as a function of the azimuthal rotation angles. The data obtained are fitted to the transformation formulae [equations (4) and (5)] by the least-squares method, as indicated by the solid lines in the figures; The two fitting parameters, α and β, which represent in the experiment, two Euler angles of the lines with respect to the (001) plane and the [1 $\bar{1}$ 0] direction, respectively, are described in Table 1. From the fitting values, the crystallographic orientations and the lengths of the lines in the sample are determined.

The results are summarized in Table 1. Dislocations A and B are both identified as the [011] direction, and their outcrops are aligned parallel to the [1 $\bar{1}$ 0] direction, indicating that the dislocations are located in the ($\bar{1}$ $\bar{1}$ 1) slip plane. Dislocation C is revealed to be parallel to the [123] direction, and it is still located in the same ($\bar{1}$ $\bar{1}$ 1) slip plane. On the other hand, the length of dislocation B is found to be 61 μm, indicating that dislocation B runs down to a depth of 43 μm below the surface along the [011] direction and bends towards dislocation C in the same slip plane.

TABLE 1

Summary of the fitting parameters, α and β and the configuration of the dislocation lines studied.

| Dislocation | α | β | Orientation | Length |
|---|---|---|---|---|
| A, B | 45° | −45° | [0 1 1] | B: 61 μm |
| C | 53.3° | −71.6° | [1 2 3] | — |
| D* | 0° | 0° | [1 $\bar{1}$ 0] | 72 μm |

*The virtual line connecting two outcrops of A and B in FIG. 3

According to this invention, an X-ray topographic technique for characterizing the three-dimensional distribution of dislocations, based on using a symmetric reflection via azimuthal rotation of a sample, is presented. This invention is a very useful tool for quantitative determination of the orientations and locations of dislocation lines in single crystals, together with two-dimensional planar distribution, depth distribution and size distribution of other structural defects.

Although an embodiment of the invention has been shown and discussed in the particular type (one-dimensional defects) of structural imperfections, the basic principle in this embodiment will be useful for various types of structural defect in a single crystal. For example it will be appreciated that this basic principle is be applicable for zero-dimensional (point), one-dimensional (line), two-dimensional (surface), and three-dimensional (volume) defects such as inclusions and voids.

The only difference according to types of defects is that in order to define the orientation and position of defects it is required to use a reference position on the surface of the sample and the corresponding image position thereof on the topograph according to each kind of defects. Then the same formula described above can be generally applied to other defects.

What is claimed is:

1. A method of determining a three-dimensional distribution of structural defects in a single crystal material, the method comprising:
   (a) disposing a single crystal sample on a holder, the sample being set to a symmetric reflection in the Bragg Geometry;
   (b) projecting a beam of incident x-rays on a predetermined crystal plane in the sample and reflecting the x-rays while the sample is azimuthally rotating with respect to an normal axis, the normal axis being perpendicular to the predetermined crystal plane;
   (c) obtaining geometrical measured values of a two-dimensional configuration of defects on the detector plane of a CCD detector; and
   (d) determining the three-dimensional distribution of the defects in the sample by formulating a geometrical relation between a three-dimensional configuration of defects on the sample and the geometrical measured values of the two-dimensional configuration of defects on the detector plane.

2. The method according to claim 1, wherein the defect includes dislocations, inclusions, or voids.

3. The method according to claim 1, wherein the three-dimensional distribution includes at least one selected from the group consisting of position, height, width, and length of the defect.

4. The method of claim 1, wherein in a projecting and reflecting step, the rotation of the sample performed by 45 degrees over a total range of 180 degrees.

5. The method according to claim 1, wherein the incident x-ray is a monochromatic beam.

6. The method according to claim 1, wherein the x-rays includes synchrotron x-ray.

7. The method according to claim 1, wherein an xyz Cartesian coordinate system is defined such that the z axis is along the diffraction vector g and the yz plane coincides with the scattering plane; wherein the three-dimensional distribution of the defect is represented by a vector u, and $$u=(\Gamma \cos \alpha \cos(\beta+\varnothing), \Gamma \cos \alpha \sin(\beta+\varnothing), -\Gamma \sin \alpha),$$

where α and β is two Euler angles at ∅=0° and Γ is a distance of the defect from a reference point; wherein a defect position measured in the detector plane is represented by a vector u', and $$u'=(\Gamma' \cos \phi, \Gamma' \sin \phi)$$

in an XY Cartesian ordinate system, where φ is an angle of the defect-to-reference line with respect to the X axis and Γ' is the length of the line; wherein, in the parallel beam approximation, $u'_x=u_x u'_y$ is equal to the projection of $u_z$ and $u_y$ onto the detection plane that is normal to the diffracted beam, u', and $$u'=(\Gamma' \cos \phi, \Gamma' \sin \phi)$$

$$=(\Gamma \cos \alpha \cos(\beta+\varnothing), \Gamma \sin \alpha \cos \theta + \Gamma \cos \alpha \sin(\beta+\varnothing)\sin \theta);$$

and wherein the angular and length components of the transformation formula, respectively are:

$$:\text{Tan } \phi = \tan \alpha \cos(\beta+\varnothing) + \tan(\beta+\varnothing)\sin \theta$$

and $$\Gamma'^2/\Gamma^2=[\cos(\beta+\varnothing)\cos \alpha]^2+[\sin \theta \sin(\beta+\varnothing)\cos \alpha + \cos \theta \sin \alpha]^2.$$

* * * * *